United States Patent [19]
Fischer, Sr.

[11] Patent Number: 6,108,582
[45] Date of Patent: Aug. 22, 2000

[54] CARDIAC PACEMAKER LEAD WITH EXTENDABLE/RETRACTABLE FIXATION

[75] Inventor: Elmar R. Fischer, Sr., Lake Jackson, Tex.

[73] Assignee: Intermedics Inc., Angleton, Tex.

[21] Appl. No.: 09/109,498

[22] Filed: Jul. 2, 1998

[51] Int. Cl.[7] ................................................ A61N 1/05
[52] U.S. Cl. ............................................................ 607/127
[58] Field of Search ............................................. 607/127

[56] References Cited

U.S. PATENT DOCUMENTS

| | | | |
|---|---|---|---|
| 4,106,512 | 8/1978 | Bisping | 128/418 |
| 4,311,153 | 1/1982 | Smits | 128/785 |
| 4,463,765 | 8/1984 | Gold | 607/127 |
| 4,567,901 | 2/1986 | Harris | 128/786 |
| 4,667,686 | 5/1987 | Peers-Travarton | 607/127 |
| 5,129,404 | 7/1992 | Spehr et al. | 128/785 |
| 5,456,708 | 10/1995 | Doan et al. | 607/127 |
| 5,545,201 | 8/1996 | Helland et al. | 607/127 |

FOREIGN PATENT DOCUMENTS

| | | | |
|---|---|---|---|
| 519053 | 10/1992 | European Pat. Off. | A61N 1/05 |
| 709111 | 7/1994 | European Pat. Off. | A61N 1/05 |

OTHER PUBLICATIONS

Intermedics, Inc., *Temporary Transcutaneous Pacing Wire Extension Lead Model 366–02*—Sales Brochure, all pages, Oct. 1982.

CPI, Inc., *Endotak C Physician's Manual*, all pages, date unknown.

*Primary Examiner*—William E. Kamm
*Attorney, Agent, or Firm*—Schwegman, Lundberg, Woessner & Kluth, P.A.

[57] ABSTRACT

A cardiac stimulator lead is provided that includes a connector for connecting to a cardiac stimulator and a tubular insulating sleeve that has a first end coupled to the connector and a second end. An electrode is coupled to the second end and has a longitudinal bore. An extendable/retractable corkscrew is positioned in the bore. In one aspect, the lead includes a radiopaque member moveable with the corkscrew to verify axial movement. In another aspect, the bore is configured so that the corkscrew will not extend fully unless tissue is present to engage the corkscrew. In another aspect, a shape-memory polymeric washer is included to restrict fluid influx after corkscrew deployment.

20 Claims, 9 Drawing Sheets

CARDIAC PACEMAKER LEAD WITH EXTENDABLE/RETRACTABLE FIXATION

BACKGROUND OF THE INVENTION

1. Field of the Invention

This invention relates generally to cardiac stimulator leads, and more particularly to a cardiac stimulator lead having an extendable and retractable screw-in fixation mechanism.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

A conventional cardiac stimulator lead normally consists of an elongated flexible tubular, electrically insulating sleeve that is connected proximally to a connector that is adapted to couple to the header of a cardiac stimulator, and distally to a tubular tip electrode. One or more ring-type electrodes may be secured to the sleeve at various positions along the length of the sleeve. The proximal end of the lead sleeve is connected to the connector by application of various biocompatible adhesives to various portions of the connector and the sleeve. The tip electrode ordinarily consists of a tubular structure that has an increased diameter portion that forms an annular shoulder against which the distal end of the lead sleeve is abutted. The exterior surface of the tubular structure is normally smooth as is the interior surface of the distal end of the lead sleeve.

In conventional active fixation tip electrodes, engagement with the endocardium is often achieved by projecting a corkscrew from the electrode. This is normally carried out by twisting the corkscrew. As the corkscrew spirals outward from the tip, the piercing point of the corkscrew pierces the endocardium, enabling the corkscrew to be screwed into the tissue by further twisting. The axial movement of the corkscrew relative to the tip electrode is usually accomplished by providing the electrode with a set of internal threads cut to match the pitch of the coils of the corkscrew. A stylet is inserted into the lead and temporarily coupled to the corkscrew. The stylet is twisted by hand to rotate the corkscrew.

Conventional open lumen leads of both the active and passive fixation varieties are subject to the influx of body fluids. Some fluid influx is usually expected, particularly in the period immediately following implantation when inflamation is most pronounced and fibrous in-growth is not established enough to provide a natural barrier to fluid flow. However, some leads are subjected to heavy influx as a result of blood disorders such as hemophilia, unexpected and prolonged inflammation, or other causes. Heavy and/or prolonged influx may harm the lead. To counter the potentially deleterious effects of fluid influx, conventional open lumen leads frequently include a washer or gasket within the tip electrode to restrict the influx of body fluids into the leads. These gaskets are molded with a central opening of fixed diameter to accommodate the corkscrew.

There are several disadvantages associated with conventional active fixation leads. It is often difficult for the implanting physician to verify both the proper deployment of a corkscrew from the tip electrode, and the successful engagement of myocardial tissue by the corkscrew. The difficulty stems from the fact that past and current corkscrews are too small to be readily perceived via fluoroscopy. In circumstances where a conventional corkscrew fails to deploy in situ and there is no visual verification of the problem, a physician may needlessly persist in twisting a stylet in an attempt to extend the corkscrew.

In addition to presenting difficulties in detecting corkscrew deployment, conventional leads do not provide visual verification of endocardial penetration by the corkscrew. The problem also stems from limitations in X-ray imaging. As a consequence, the most common method of verifying a proper engagement of the endocardium by the corkscrew is by touch. Following deployment of the corkscrew, the physician applies a gentle, axial, tensile force on the lead connector. An absence of appreciable longitudinal movement of the lead is an indication that the corkscrew has successfully penetrated and engaged the tissue. However, a sudden longitudinal movement of the lead is an indication that the corkscrew either did not engage enough tissue or did not engage any tissue at all. In such circumstances, the physician must retract the corkscrew, reposition the tip of the lead proximate the targeted tissue, and redeploy the corkscrew. This process may be very time consuming, particularly where very precise electrode positioning is medically indicated and the targeted tissue is difficult to reach, e.g. requires complex bending and manipulation of the stylet.

The problem of tissue engagement verification may be aggravated by other aspects of conventional tip electrode and corkscrew design. In most conventional leads, the corkscrew is deployed by a set of internal threads in the tip electrode. The threads extend from some point within the electrode to the opening at the distal end of the electrode from which the corkscrew deploys. A by-product of this design is that the corkscrew deploys as soon as the stylet is twisted. This may not be problematic where the tip is positioned and maintained in close contact with the targeted tissue. However, if the tip is not bearing directly against the targeted tissue or not positioned within a fraction of the total length of the corkscrew at the time the stylet is twisted, the corkscrew may deploy and either not engage any tissue at all or only penetrate a small distance into the tissue. In the former situation, the corkscrew will have to be retracted and second attempt made. In the latter scenario, two undesirable outcomes may result. First, a less than optimum amount of tissue penetration may result. Second, minimal tissue penetration by a fully extended corkscrew may result in the conducting tip of the electrode having only intermittent physical contact with the targeted tissue or no contact at all.

As noted above, many conventional leads incorporate a washer. A drawback associated with conventional washer design is fixed aperture size. Where, as is often the case, the washer is coaxially located with the corkscrew, the aperture must be made large enough to accommodate the outer diameter of the corkscrew. While such washers provide some restriction to fluid influx, their capability in this regard is limited by their permanently sized apertures.

The present invention is directed to overcoming or reducing the effects of one or more of the foregoing disadvantages.

SUMMARY OF THE INVENTION

In accordance with one aspect of the present invention, a cardiac stimulator lead is provided. The lead includes a connector for connecting to a cardiac stimulator and a tubular insulating sleeve that has a first end coupled to the connector and a second end. An electrode is coupled to the second end and has a longitudinal bore. A washer is disposed in the bore for restricting the influx of body fluids into the sleeve. The washer has an aperture defining a rim, and is composed of a shape-memory polymeric material deformable in situ from a temporary shape to a permanent shape whereby the area of the aperture is reduced in situ. A conductor wire is disposed in the sleeve and coupled between the connector and the electrode for transmitting electric signals between the cardiac stimulator and the electrode.

In accordance with another aspect of the present invention, a cardiac stimulator lead is provided. The lead includes a connector for connecting to a cardiac stimulator. The connector has a pin member rotatably coupled thereto. A tubular insulating sleeve has a first end coupled to the connector and a second end. An electrode is coupled to the second end and has a longitudinal bore. A corkscrew is coupled to the electrode and is projectable from and retractable into the bore. A portion of the electrode is radiopaque. The lead includes means for transmitting torque from the pin member to the corkscrew. A radiopaque member is coupled to the corkscrew. A conductor wire is disposed in the sleeve and coupled between the connector and the electrode for transmitting electric signals between the cardiac stimulator and the electrode.

In accordance with another aspect of the present invention, an apparatus is provided. In a cardiac stimulator lead that has a tubular electrode, the apparatus includes a washer disposed in the electrode for restricting the influx of body fluids therein. The washer has an aperture defining a rim, and is composed of a shape-memory polymeric material deformable in situ from a temporary shape to a permanent shape whereby the area of the aperture is reduced in situ.

In accordance with still another aspect of the present invention, a tip electrode for a cardiac lead is provided. The tip electrode includes a tubular shank having a longitudinal bore extending therethrough. The bore has a first longitudinal section that has at least one internal thread and a second longitudinal section. A corkscrew is disposed in the bore and has a first range of axial movement wherein the at least one internal thread is engaged, and a second range of axial movement wherein the at least one internal thread is not engaged. A portion of the corkscrew projects from the second longitudinal portion in the second range of axial movement. The tip includes means for rotating the corkscrew to move the corkscrew axially while in the first range of axial movement and to screw the corkscrew into myocardial tissue while in the second range of axial movement.

In accordance with another aspect of the present invention, a cardiac stimulator lead is provided. The lead includes a connector for connecting to a cardiac stimulator and a tubular insulating sleeve that has a first end coupled to the connector and a second end. An electrode is coupled to the second end and has a longitudinal bore extending therethrough. The bore has a first longitudinal portion that has at least one internal thread and a second longitudinal portion. A corkscrew is disposed in the bore. The corkscrew has a first range of axial movement wherein the at least one internal thread is engaged, and a second axial range of axial movement wherein the at least one internal thread is not engaged. A portion of the corkscrew projects from the second longitudinal portion in the second range of axial movement. The lead includes means for rotating the corkscrew to move the corkscrew axially while in the first range of axial movement and to screw the corkscrew into myocardial tissue while in the second range of movement. A conductor wire is disposed in the sleeve and coupled between the connector and the electrode for transmitting electric signals between the cardiac stimulator and the electrode.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
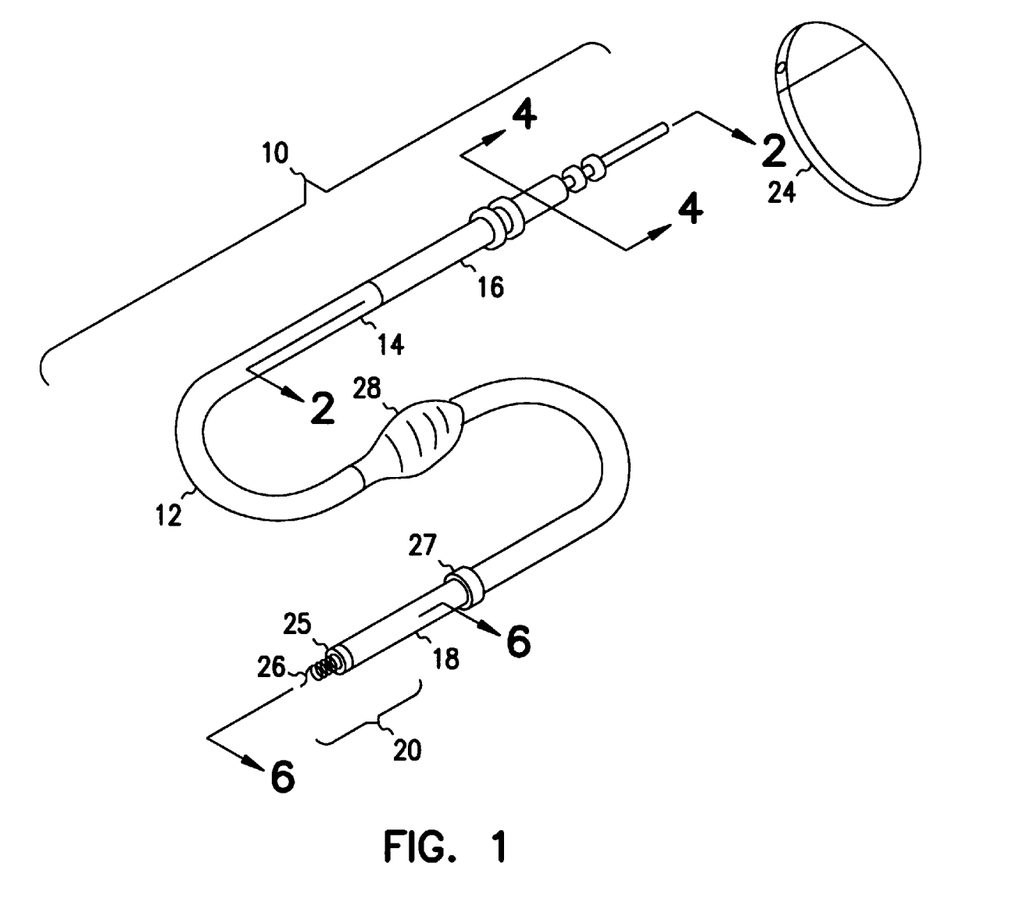
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac stimulator lead 10 that includes a flexible insulating sleeve 12 that has a proximal end 14 coupled to a connector 16, and a distal end 18 coupled to a tip electrode 20. The connector 16 is designed to be inserted into a cardiac stimulator 24, and is shown highly exaggerated in size relative to the cardiac stimulator 24. The cardiac stimulator 24 may be a pacemaker, a cardioverter/defibrillator, or other type of stimulator or a sensing instrument. The tip electrode 20 includes a tip 25 and a corkscrew 26 projectable therefrom to engage and actively secure the lead 10 to myocardial tissue. The illustrated embodiment of the lead 10 is bipolar. Accordingly, the distal end 18 is provided with an electrode 27 located proximal to the tip electrode 20. However, unipolar or other multi-polar arrangements are possible as well. A suture sleeve 28 is slipped over the sleeve 12. During implantation, the suture sleeve 28 is sewn to body tissue at the site of transvenous entry.

The sleeve 12 is a flexible tubular member that provides a robust, electrically insulating coupling between the connector 16 and the electrode 20. The sleeve 12 protects one or more fine gage conductor wires enclosed therein from body fluids and tissues, and is advantageously composed of a biocompatible, electrically insulating material, such as silicone, polyurethane, or like materials.

Figure 2:
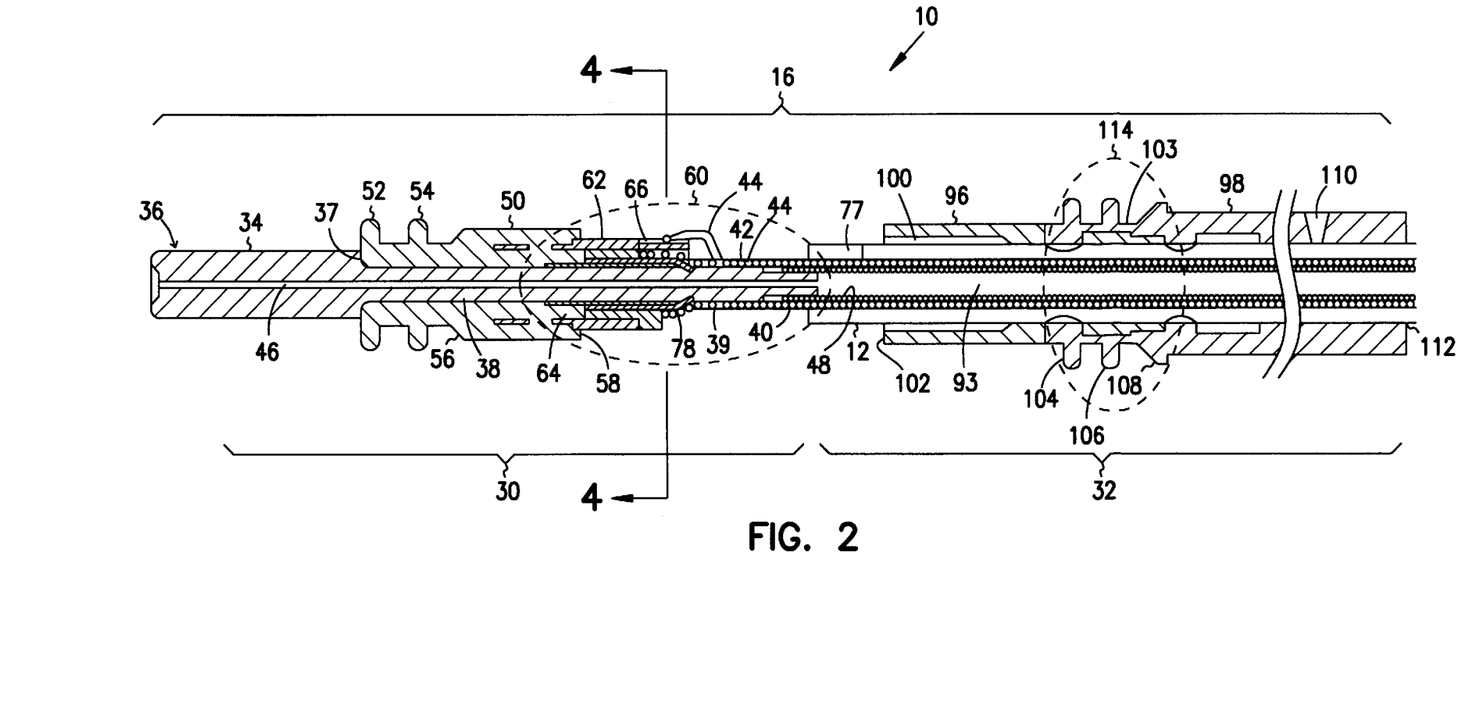
FIG. 2 is a cross-sectional view of the cardiac lead of FIG. 1 taken at section 2—2 in accordance with the present invention.

The detailed structure of the connector 16 may be understood by referring now to FIG. 2, which is a cross-sectional view of FIG. 1 taken at section 2—2. The connector 16 includes a connector pin assembly 30 coupled to a connector sleeve assembly 32. For clarity of illustration, the connector pin assembly 30 and the connector sleeve assembly 32 are shown exploded. The connector pin assembly 30 includes a tubular pin member 34 that has an elongated proximal end 36 designed to make electrical contact with one or more electrical contacts inside the cardiac stimulator 24 depicted in FIG. 1, and serves as a handle for twisting the pin 34 to manipulate the corkscrew 26 as described below. The distal end of the pin 34 consists of an intermediate shank 38 that tapers down from the proximal end 36 to establish an annular shoulder 37, an intermediate shank 39, and a distal shank 40. The intermediate shank 39 is suitably sized to accommodate the nested coils of a conductor wire 42 and another conductor wire 44. The distal shank 40 is sized to receive the coils of a torque coil 48. The wire 42 is electrically connected distally to the tip electrode 20 depicted in FIG. 1, and the wire 44 is electrically connected distally to the annular electrode 27 depicted in FIG. 1. The connections of the wires 42 and 44 to the pin assembly 30 will be described in more detail below. A lumen 46 extends through the pin member 34.

A first insulating sleeve 50 is coupled to the exterior of the pin member 34. The first insulating sleeve 50 includes longitudinally spaced-apart O-rings 52 and 54 that are designed to engage structures within the cardiac stimulator 24 shown in FIG. 1 and to provide a seal for the pin member 34 against the intrusion of body fluids following implantation. A single O-ring may be used in place of the pair 52 and 54. The first insulating sleeve 50 is provided with a proximally facing chamfer surface 56 that is principally designed to provide a tapered surface to facilitate easy insertion of the connector 16 into the cardiac stimulator 24 shown in FIG. 1. The distal end of the first insulating sleeve 50 includes a distally facing annular surface 58 against which the conductor sleeve assembly 32 is abutted when the connector 16 is assembled. The first insulating sleeve 50 is advantageously composed of a biocompatible flexible material that may be advantageously injection molded around the pin member 34. The material may be silicone, polyurethane, or like materials. In this way, the O-rings 52 and 54 may be formed integrally with the first insulating sleeve 50. Alternatively, the first insulating sleeve 50 may be provided with external grooves and the O-rings 52 and 54 secured to the first insulating sleeve 50 as separate members.

Figure 3:
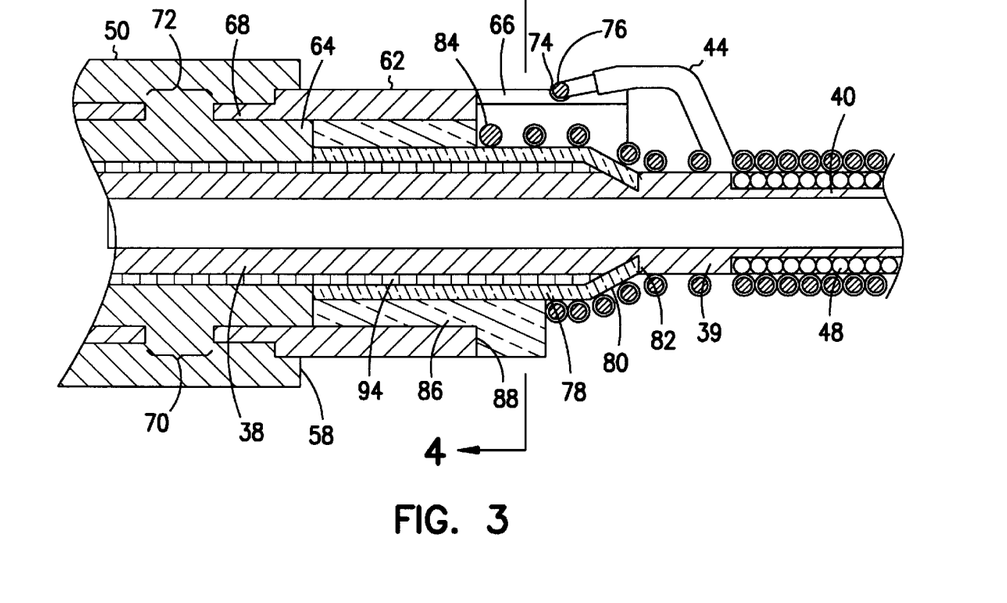
FIG. 3 is a close-in view of a portion of the lead shown in FIG. 2 depicting the rotatable pin member in accordance with the present invention.
Figure 4:
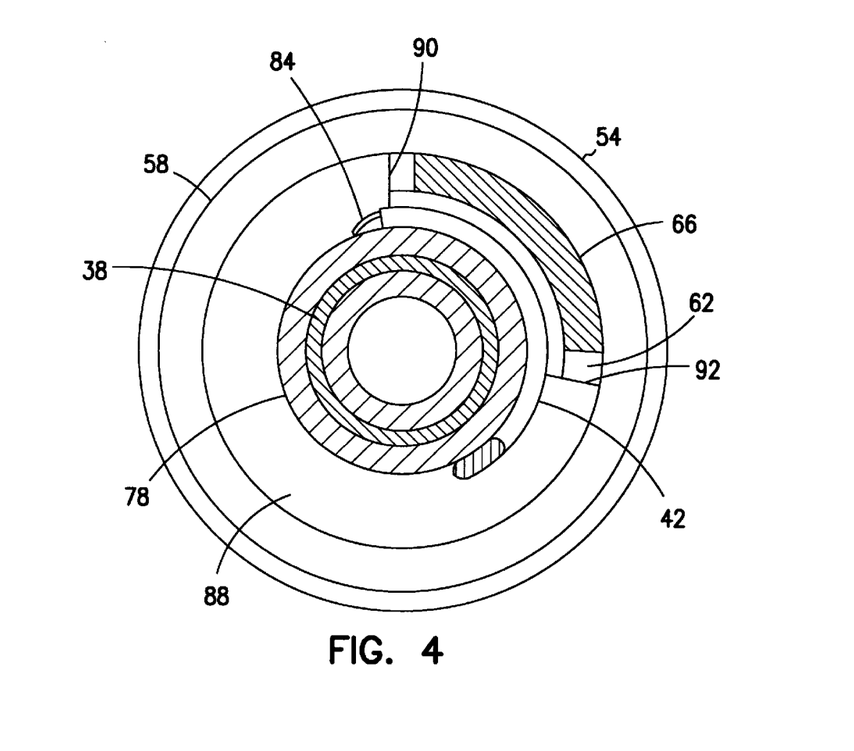
FIG. 4 is a cross-sectional view of FIGS. 2 and 3 taken at section 4—4 in accordance with the present invention.

Referring now also to FIG. 3, which is a detailed view of the portion of FIG. 2 circumscribed by the dashed oval 60, and to FIG. 4, which is a cross-sectional view of FIG. 3 taken at section 4—4, an annular member 62 is disposed around a reduced diameter portion 64 of the sleeve 50. The annular member 62 includes a distally projecting flag 66 to which the conductor wire 44 is attached and which provides an electrical pathway between the wire 44 and a contact (not shown) within the cardiac stimulator 24 shown in FIG. 1. The annular member 62 includes a proximally projecting reduced diameter nipple 68 that projects into the first insulating sleeve 50. The nipple has two or more circumferentially spaced ports 70 and 72 that enable molded structure to harden therein and provide a secure mechanical engagement between the first insulating sleeve 50 and the annular member 62. The flag 66 is provided with an external circumferential groove 74 that is dimensioned to receive the stripped end 76 of the conductor wire 44. The stripped end 76 is secured to the flag 66 by laser welding or like welding techniques.

As best seen in FIG. 2, the sleeve 12 is provided with a longitudinally extending slot 77 that is slightly wider than the outer diameter of the wire 44. The slot 77 provides a space to accommodate the wire 44 so that the sleeve 12 may be pushed past the wire 44 and abutted against the reduced diameter portion 64.

Electrical connection between the conductor wire 42 and the pin member 34 is established by a cylindrical contact sleeve 78 through which the pin member 34 is journalled and which is disposed partially within the annular member 62. The contact sleeve 78 abuts proximally against the reduced diameter portion 64 and is provided distally with an inwardly tapering portion 80 that engages a notch in the pin member 34 at 82. The engagement between the tapered portion 80 and the notch 82 serves to retain the pin member 34 within the connector pin assembly 30. As discussed more below, the pin member 34 is rotated to extend and/or retract the corkscrew 26 depicted in FIG. 1. The skilled artisan will appreciate that if the conductor wire 42 is allowed to rotate with the pin member 34, the wire 42 may become damaged or provide undesirable resistance to the rotation of the pin member 34. Accordingly, the fit provided between the tapered portion 80 and the notch 82 is such that the pin member 34 may readily be rotated relative to the fixed contact sleeve 78 while still maintaining sufficient contact between the pin member 34 and the contact sleeve 80 such that electrical conductivity between the conductor wire 42 and the pin member 34 is retained. As best seen in FIG. 4, the wire 42 is stripped at 84 and secured to the contact sleeve 78 by laser welding or like techniques. Electrical isolation between the annular member 62 and the contact sleeve 78 is provided by an annular bushing 86 that includes distally disposed annular flange 88 shoulders against the distal end of the annular member 62. The flange is not coextensive with the entire circumference of the bushing 86. Instead, the flange 88 includes a cutout, best seen in FIG. 4, extending from the surface 90 to the surface 92. The cutout is provided to accommodate the flag 66.

The embodiment depicted in FIGS. 1, 2, 3, and 4, is bipolar. However, a unipolar arrangement may be implemented by incorporating a single conductor wire, such as the wire 42, that is coupled to either the pin member 34 or to the flag 66. Similarly, the conductor wires 42 and 44 are depicted as single individually insulated wires with insulation stripped prior to welding to contact sleeve 68 and the flag 66. However, the skilled artisan will appreciate that the conductor wires 42 and 44 may not be individually insulated if the lead 10 is unipolar or if the various conductor wires in the lead 10 are coaxially arranged or arranged in a nested configuration.

Referring again specifically to FIGS. 2 and 3, the torque coil 48 is secured to the distal shank 40 by laser welding or like welding techniques. The pitch of the individual coils in the torque coil 48 is largely a matter of design discretion. The skilled artisan will appreciate that as the pitch of the coils is increased, the torque carrying capabilities of the coil 48 will decrease unless the stiffness of the material used to fabricate the coil 48 is proportionally increased. The torque coil 48 is advantageously composed of a biocompatible material with sufficient stiffness to readily transmit torque from the pin member 34 to the corkscrew 26 depicted in FIG. 1. Exemplary materials include MP35N alloy, 316L stainless steel, or like materials. The torque coil 48 and the wires 42 and 44 extend longitudinally through the lumen 93 of the sleeve 12 to the tip electrode 20.

It is desirable to electrically isolate the annular member 62 from the pin member 34 to alleviate the potential for short circuiting. This is particularly important during electrical verification testing, which is normally done at relatively high voltage. The primary electrical insulation is provided by the first insulating sleeve 50, and particularly the reduced diameter portion 64, as well as the bushing 86. It is anticipated that the material used to fabricate the first insulating sleeve 50 will readily fill the space, and provide a complete electrically insulating separation between the annular member 62 and the pin member 34. However, the skilled artisan will appreciate that there is the possibility of void formation during the molding process due to air bubbles or other mechanisms. If a void is formed in the reduced diameter portion 64 between the annular member 62 and the pin member 34, destructive arcing may occur in the void during high voltage electrical verification testing of the lead 10. To reduce the possibility of shorts through a void formed in the reduced diameter portion 64, an insulating annular member 94 may be slipped over the intermediate shank 38 and abutted proximally against the shoulder 37 prior to molding of the first insulating sleeve 50. The insulating annular member 94 may be composed of a variety of biocompatible insulating materials such as, for example, polyimide, polyurethane, or like materials.

Referring again to FIG. 2, the connector sleeve assembly 32 includes a conductor sleeve 96 that is coupled to a second insulating sleeve 98. The second insulating sleeve 98 is a tubular member of such length and the scale of FIG. 2 is such that the second insulating sleeve 98 is shown broken. The conductor sleeve 96 includes a proximally disposed bore 100 that is dimensioned so that the conductor sleeve 96 may be readily slipped over the annular member 62 until the annular surface 102 of the conductor sleeve 96 abuts the annular shoulder 58 of the first insulating sleeve 50. The conductor sleeve 96 is designed to establish an electrical pathway between the annular member 62 and a conducting structure inside the cardiac stimulator 24 shown in FIG. 1. Accordingly, the fit between the internal diameter of the conductor sleeve 96 and the outer diameter of the annular member 62 should be close enough to provide good electrical contact. The conductor sleeve 96 is coupled to the annular member 62 by laser welding or like techniques.

The proximal end 103 of the second insulating sleeve 98 is provided with two longitudinally spaced-apart O-rings 104 and 106 that serve to seal the conductor sleeve 96 against the intrusion of body fluids after the lead 10 is coupled to the cardiac stimulator 24 shown in FIG. 1. As with the aforementioned O-rings 52 and 54, the O-rings 104 and 106 may be integrally molded into the second insulating sleeve 98 or attached as separate members. On the distal side of the O-ring 106, the second insulating sleeve 98 expands in diameter and defines a chamfer surface 108 that provides the same functionality as the chamfer surface 56, albeit in conjunction with a different portion of the internal structure of the cardiac stimulator 24 shown in FIG. 1. The internal diameter of the second insulating sleeve 98 is generally dimensioned to provide a sliding fit with the outer surface of the sleeve 12 to permit easy assembly. The second insulating sleeve 98 is secured to the sleeve 12 by a suitable biocompatible medical grade adhesive, such as silicone, or any of a variety of two stage adhesives. To facilitate the introduction and spreading of the adhesive, the second insulating sleeve 98 is provided with a port 110. Adhesive is introduced into the port 110 under slight pressure to encourage the rapid and uniform spreading of the adhesive around the sleeve 12. The flow characteristics of the adhesive may be enhanced by thinning with a suitable diluent, such as heptane, prior to injection through the port 110. In addition, adhesive is back filled between the second insulating sleeve 98 and the sleeve 12 by injection under slight pressure at the interface designated 112.

Figure 5:
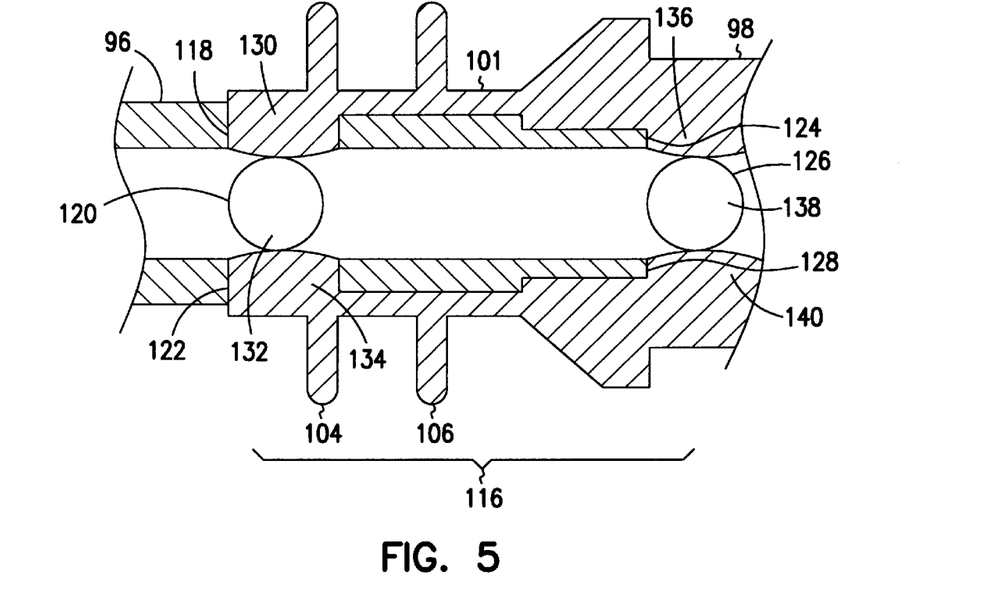
FIG. 5 is a close-in view of a portion of the lead shown in FIG. 2 depicting another portion of the connector in accordance with the present invention.

The connection between the conductor sleeve 96 and the second insulating sleeve 98 may be more readily understood by referring now to FIG. 5, which is a magnified view of the portion of FIG. 2 circumscribed by the dashed oval 114. Note that in FIG. 5, the sleeve 12 is not shown for clarity of illustration. A central portion 116 of the conductor sleeve 96 is provided with a plurality of circumferentially spaced bores, six of which are depicted at 118, 120, 122, 124, 126, and 128. The bores 118, 120, 122, 124, 126, and 128 are designed to enable the material used to mold the second insulating sleeve 98 to flow into the bores 118, 129, 122, 124, 126, and 128 and harden into buttons 130, 132, 134, 136, 138, and 140. The engagement between the buttons 130, 132, 134, 136, 138, and 140 and the central portion 116 of the conductor sleeve 96 establishes a secure mechanical engagement between the conductor sleeve 96 and the second insulating sleeve 98. The second insulating sleeve 98 is advantageously composed of the same types of materials used to fabricate the first insulating sleeve 50 shown in FIG. 2, and is advantageously injection molded.

The pin member 34, the annular member 62, and the conductor sleeve 96 are advantageously composed of a biocompatible conducting material that may be welded via laser or like techniques. Exemplary materials include 316L stainless steel, other suitable types of stainless steel, MP35N, or like materials.

The connector 16 depicted in FIGS. 1, 2, 3, 4, and 5, eliminates the necessity for the conventionally used tubular crimping members and the attendant difficulties in establishing consistent and reliable crimped connections between the conductor wires of the lead and the various crimping members. Reliable electrical and mechanical connection between the conductor wires 42 and 44 and the connector 16 are established by welding. The use of welded connections in lieu of crimping tubes or slugs permits interim inspection and testing of the wire-to-connector connections and more rapid assembly.

Figure 6:
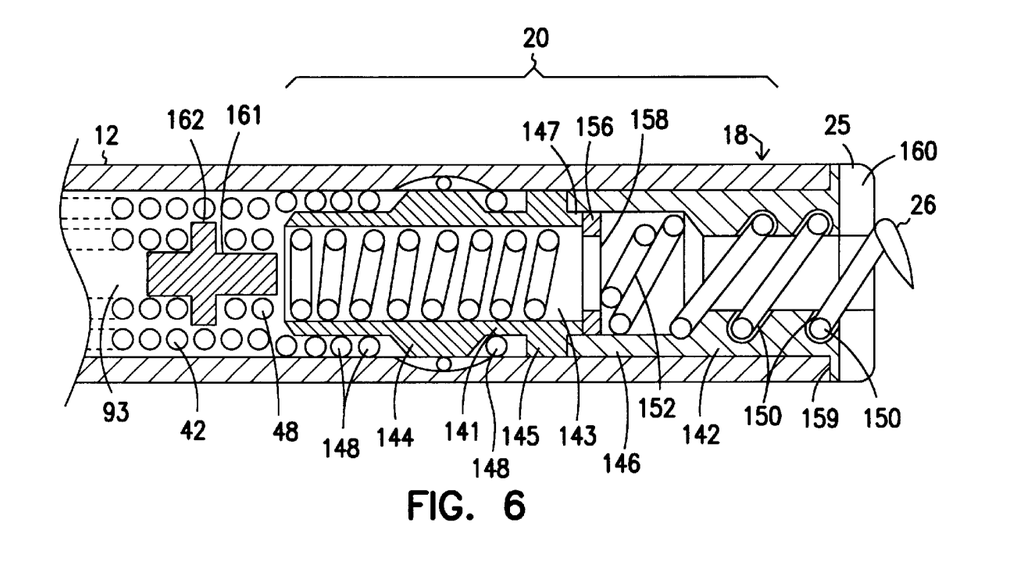
FIG. 6 is a cross-sectional view of FIG. 1 taken at section 6—6 in accordance with the present invention.
Figure 7:
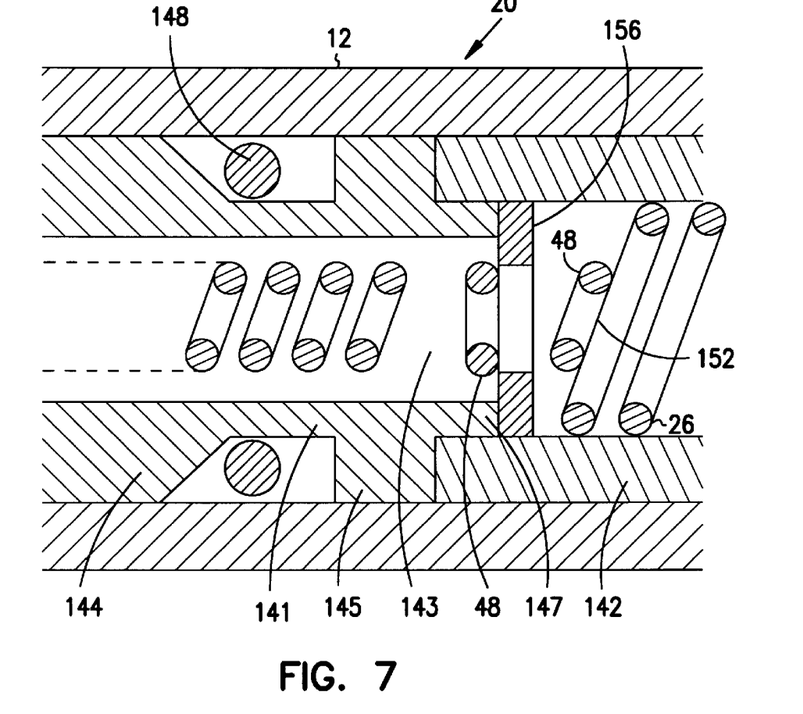
FIG. 7 is a close-in view of a portion of the electrode shown in FIG. 6 in accordance with the present invention.

The detailed structure of the tip electrode 20 may be understood by referring now to FIG. 6, which is a cross-sectional view of FIG. 1 taken at section 6—6, and to FIG. 7, which is a detailed view of a portion of FIG. 6. The electrode 20 consists of a tubular shank 141 coupled to another tubular shank 142 and sharing a common, centrally disposed bore 143. The shank 141 includes a proximally disposed flange 144 and a distally positioned flange 145. The flange 145 abuts the proximal end 146 of the shank 142, and terminates short of the distal end of the shank 141 so that a distally facing annular shoulder 147 projects into the shank 142. Alternatively, the structure of the shanks 141 and 142 may be incorporated into a single piece.

The distal coils 148 of the conductor wire 42 are spiraled around the shank 141 so that at lease one coil 148 is disposed between the flange 144 and the flange 145. This provides a mechanical capture of the coil or coils 148 to secure the wire 42 to the shank 141. The wire 42 is stripped distally to establish a conductive path to the shank 141. The wire 42 may also be secured by laser welding, other like welding techniques, or other suitable fastening methods. The main body of the shank 141 is provided with an outer diameter that is slightly larger than the inner diameter of the coils 148 of the wire 42, but smaller than that of the flanges 144 and 145. The distal coils 148 may be connected to the shank 141 by first urging the coils 148 over the main body of the shank 144 and then over the flange 144, and finally by welding, if desired.

The shank 142 is provided with a set of internal grooves or threads 150 dimensioned to receive the corkscrew 26, which is shown in a partially extended position in FIG. 6. The corkscrew 26 is connected proximally to the torque coil 48 at 152 by laser welding or like techniques. Rotation of the torque coil 48 causes the corkscrew 26 to rotate. As the corkscrew 26 rotates, the threads 150 urge the corkscrew 26 to extend from or retract into the bore 143, depending on the direction of rotation and the type of threads, i.e., left or right handed. The number of threads is a matter of discretion.

An annular washer 156 having a central aperture 158 is disposed inside the shank 142 and abutted against the annular shoulder 147 of the shank 141. The washer 156 is designed to provide some restriction to the influx of body fluids into the lumen 93 of the sleeve 12. The washer 156 may be composed of a variety of biocompatible flexible materials, such as, silicone, polyimide, or like materials. The aperture 158 is provided and sized to accommodate the torque coil 48.

The shanks 141 and 142 are inserted into the distal end 18 of the sleeve 12. The tip 25 of the shank 142 is provided with an expanded diameter to establish a proximally facing annular shoulder 159 against which the distal end 18 is abutted. To secure the electrode 20 to the sleeve 12, a biocompatible adhesive is applied to the exterior of the shanks 141 and 142 prior to insertion into the distal end 18 of the sleeve 12. The adhesive may be a suitable medical grade adhesive, such as silicone based adhesive, a two-part adhesive, or similar adhesives. The electrical transmission capability of the tip 25 is enhanced by increasing the surface thereof exposed to myocardial tissue. In this regard, one or more slots 160 are provided in the face of the tip 25.

The shank 142 may be fabricated from a variety of biocompatible conducting materials, such as iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material.

It is desirable for the implanting physician to be able to readily verify deployment of the corkscrew 26 during implantation. In conventional lead designs, this task is often difficult due to the lack of radiopacity of conventional corkscrews. To alleviate this difficulty, a portion of the electrode 20 is composed of a suitable biocompatible radiopaque material, such as, platinum iridium alloy (90% platinum, 10% iridium, or other suitable radiopaque material. In this example, the shank 141 is composed of radiopaque material. The shank 141 thus provides a radiopaque marker of fixed position, that is, fixed relative to the sleeve 12 and the electrode 20, and as such, serves as a position benchmark. In addition, a radiopaque member or slug 161 is coupled to the torque coil 48, and thus to the corkscrew, by nesting the slug 161 inside the coil 48 as shown, or by making the slug 161 tubular and nesting it around the torque coil 48. In the embodiment illustrated in FIG. 6, the slug 161 consists of a cylindrical member having a radially outwardly projecting flange 162 that is disposed between adjacent coils of the torque coil 48 and provides a means of preventing the slug 161 from moving axially independently of the coils 48. If desired, the slug 161 may also be welded to the torque coil 48.

Prior to manipulation of the torque coil 48 to extend or retract the corkscrew 26, the initial axial separation of the slug 161 and the shank 141 may be readily determined via fluoroscopy. During extension or retraction, the torque coil 48 is rotated resulting in an axial movement of the corkscrew 26, and both the torque coil 48 and the slug 161 while the shank 141 remains fixed. The change in axial spacing between the slug 161 and the shank 141 may be easily observed under fluoroscopy. Thus, a ready method of quickly verifying the extension and/or the retraction of the corkscrew 26 is provided.

The extension and retraction operations of the lead 10 may be understood by referring now to FIGS. 1, 2, and 6. The lead 10 is implanted endocardially and the electrode 20 is positioned proximate the targeted myocardial tissue, typically by using a stylet (not shown) that is inserted through the pin member 34 and advanced down the lumen 93 of the sleeve 12. Through a combination of axial force applied on the proximal end of the lead 10 and manipulation of the stylet, the tip 25 is brought into physical engagement with myocardial tissue. To extend the corkscrew 26 and engage the myocardial tissue, the pin member 34 is twisted by hand either clockwise or counterclockwise, depending upon whether the grooves in the shank 144 are right-handed or left-handed. Torque transmitted to the pin member 34 by hand is, in turn, transmitted to the corkscrew 26 via the torque coil 48. Extension of the corkscrew 26 out of the shank 144 may be verified through fluoroscopy or other imaging techniques by observing the movement of the radiopaque slug 161 in relation to the shank 141. After the corkscrew 26 has been fully extended, successful engagement with myocardial tissue may be verified by applying a gentle axial force to the connector by hand. An unsuccessful fixation with myocardial tissue may be determined via imaging as well as a sudden axial movement of the lead 10 in response to the applied axial force. To retract the corkscrew 26, the pin member 34 is twisted in the opposite direction.

Figure 8:
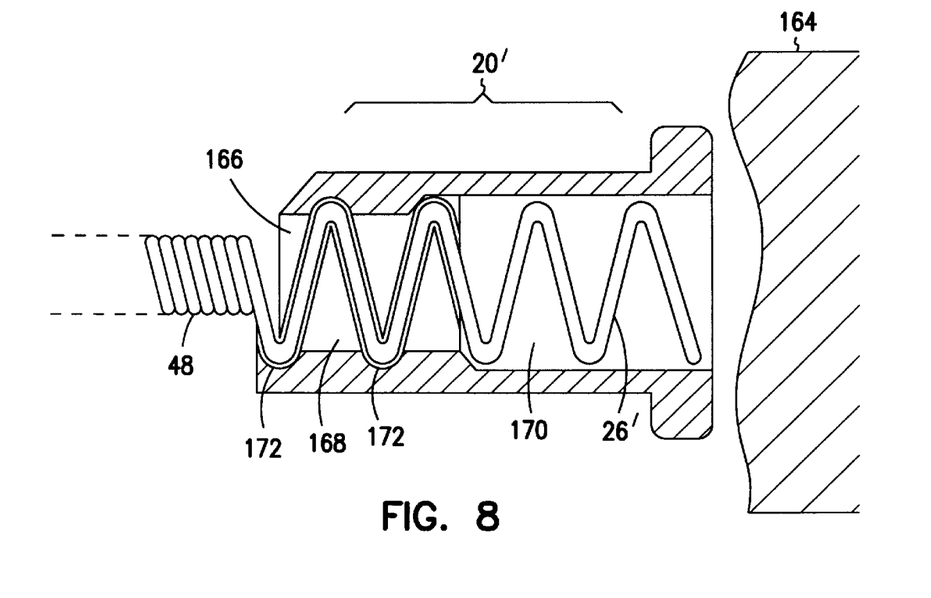
FIG. 8 is a cross-sectional view like FIG. 6 of an alternate tip electrode embodying a "smart" corkscrew in accordance with the present invention.
Figure 9:
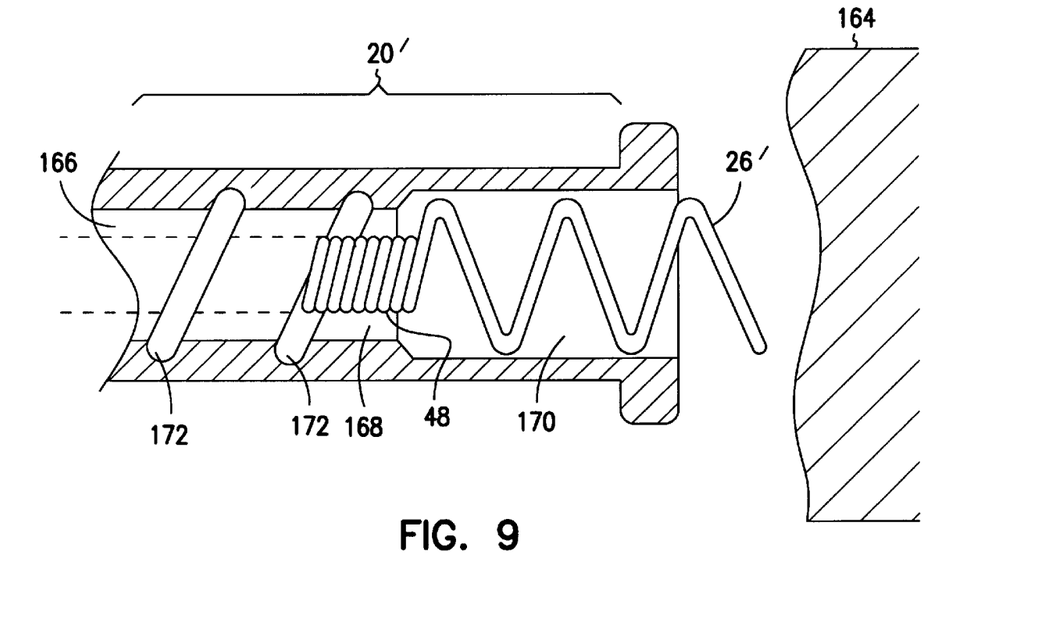
FIG. 9 is a cross-sectional view like FIG. 7 depicting partial extension of the "smart" corkscrew in accordance with the present invention.
Figure 10:
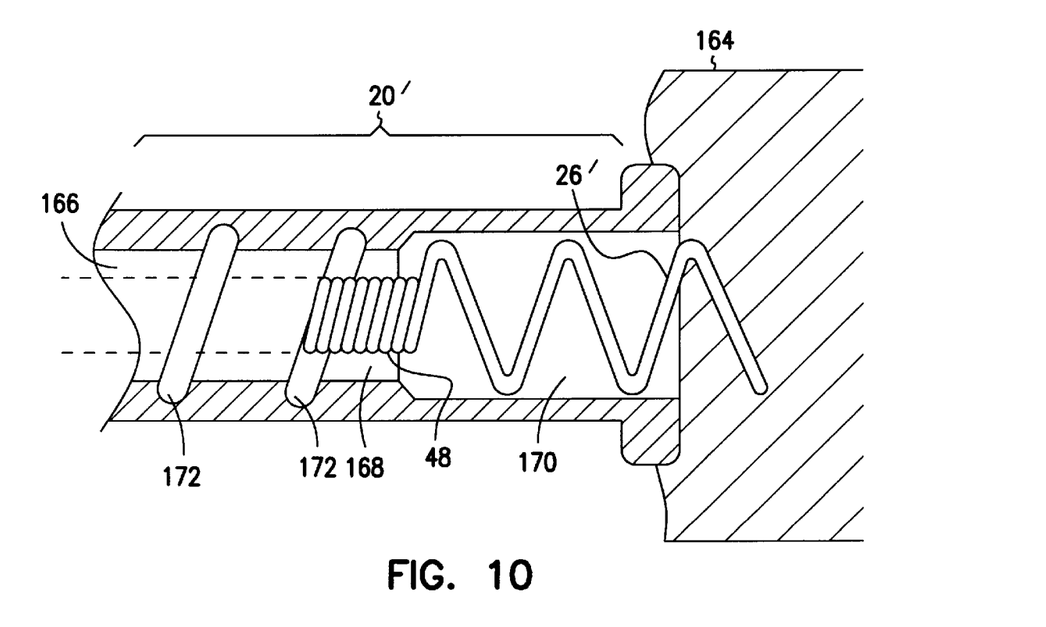
FIG. 10 is a cross-sectional view like FIG. 7 depicting partial extension of the "smart" corkscrew in accordance with the present invention.

In an alternate embodiment depicted in FIGS. 8, 9, and 10, the tip electrode, now designated 20', is provided with a "smart" corkscrew, now designated 26'. The term "smart" refers to the ability of the corkscrew 26' to fully deploy only in circumstances where the corkscrew 26' is firmly engaging and penetrating myocardial tissue 164. FIG. 8 depicts the electrode 20' with the corkscrew 26' in a fully retracted position. The electrode 20' is a tubular member provided with a longitudinally disposed lumen 166 that is divided into two sections, a first longitudinal or threaded section 168, and a second longitudinal or smooth section 170. In the threaded section 168, the electrode 20' is provided with a set of internal threads or grooves 172 that are configured similarly or identically to the grooves 150 depicted in FIG. 6. The corkscrew 26' has a first range of axial movement while engaged by the threads 172. The number of threads 172 is a matter of design discretion, though at least one is necessary to move the corkscrew 26' axially.

The smooth, i.e., unthreaded, section 170 is provided with an internal diameter that is larger than the outer diameter of the corkscrew 26' and has a relatively smooth bore to enable the corkscrew 26' to pass therethrough with little or no interference. The corkscrew 26' has a second range of axial movement where the threads 172 are not engaged.

The torque coil 48 is coupled proximally to the corkscrew 26' as described above. If a portion of the corkscrew 26' is in physical engagement with the grooves 172, as is the case in FIG. 8, torque applied to the corkscrew 26' via the torque coil 48 will produce an axial movement of the corkscrew 26' as generally described above.

The operation of this embodiment may be understood by referring now to FIGS. 9 and 10. The electrode 20' is implanted and positioned proximate myocardial tissue 164 generally as described above. Through manipulation of the torque coil 48, the corkscrew 26' is moved axially through the first range of axial movement from the fully retracted position depicted in FIG. 8 to the partially extended position shown in FIG. 9. In the partially extended position shown in FIG. 9, the corkscrew 26' has moved axially so that no portion of the corkscrew 26' is in physical engagement with the grooves 172. At this stage, the corkscrew 26' is in the second range of axial movement, and continued twisting of the torque coil 48 will simply rotate the corkscrew 26' and will not appreciably advance the corkscrew 26' axially. However, as shown in FIG. 10, when the electrode 20' is brought into physical contact with the myocardial tissue 164, further twisting of the torque coil 48 will result in the corkscrew 26' engaging and penetrating the myocardial tissue 164 axially. In this way, the corkscrew 26' will only project significantly from the electrode 20' when the corkscrew 26' is in physical engagement with myocardial tissue 164. The electrode 20' eliminates the time consuming task of retracting the corkscrew 26' into the electrode 20' by twisting the torque coil 48 in circumstances where the corkscrew 26' did not successfully engage the myocardial tissue 164 and where another attempt to attach the electrode 20' to the myocardial tissue is contemplated.

Figure 11:
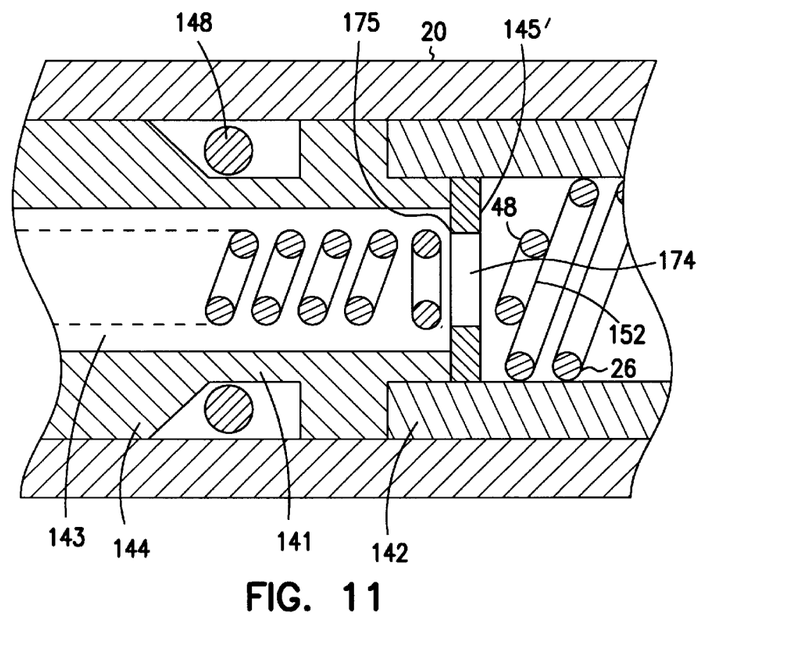
FIG. 11 is a cross-sectional view like FIG. 7 of a portion of a tip electrode incorporating a washer composed of a shape-memory polymeric material in accordance with the present invention.
Figure 12:
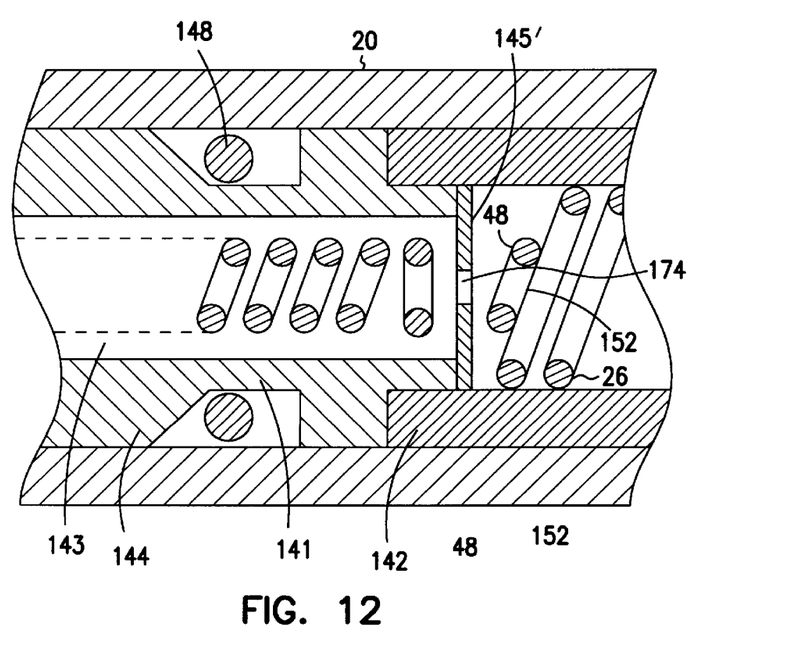
FIG. 12 is a cross-sectional view depicting in situ deformation of the washer of FIG. 11 in accordance with the present invention.
Figure 13:
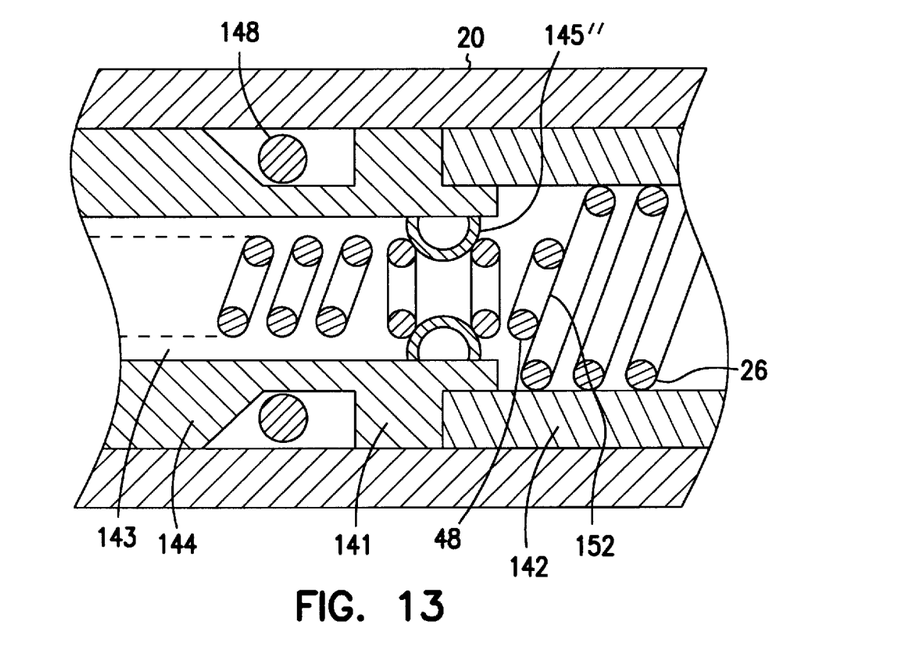
FIG. 13 is a cross-sectional view like FIG. 11 of an alternate shape-memory washer following in situ deformation in accordance with the present invention.

FIGS. 11, 12, and 13 are views of scope similar to FIG. 7, but depict alternate embodiments incorporating a washer composed of a heat sensitive shape-memory polymeric material. In the embodiment depicted in FIGS. 11 and 12, the washer is designated 145'. In the embodiment shown in FIG. 13, the washer is designated 145". A heat-sensitive shape-memory polymeric material behaves generally like a rigid material while at temperatures below the glass transition temperature $T_g$, but undergoes significant softening and may be readily plastically deformed when heated above $T_g$. When the material is then cooled below $T_g$, the deformation is fixed and the shape remains stable. However, the original shape of the material may be recovered by reheating the material above $T_g$.

Turning initially to FIGS. 11 and 12, the washer 145' is first molded into the permanent shape shown in FIG. 12 during production. The washer 145' is advantageously molded with an aperture 174 that has a permanent inner diameter that will significantly restrict the influx of body fluids. The aperture defines a rim 175. A variety of well known molding techniques may be used to create the washer 145', such as injection molding, extrusion molding, or like techniques. The molding process subjects the heat-sensitive shape-memory polymeric material to a temperature well in excess of the $T_g$ for the material for a sufficient time to form the washer 145' into the permanent shape. Thereafter, the washer 145' may be deformed into the temporary shape shown in FIG. 11 by deforming the washer 145' at a temperature above $T_g$, and maintaining the washer 145' in the temporary shape while the temperature is lowered below $T_g$. After cooling below $T_g$, the washer 145' retains the temporary shape. However, if the washer 145' is later heated above $T_g$, it will deform substantially back into the permanent shape in which it was originally molded. In this way, the washer 145' may be initially produced with a permanent shape that has a very small inner diameter aperture 174.

Where molding of the desired permanent shape is difficult in view of the molding process used and the small dimensions of the washer 145', the washer 145' may be molded with a first permanent shape that best suits the molding process. This may be, for example, a shape with a larger than desired permanent diameter. Thereafter, the washer 145' may be provided with a new permanent shape by heating the washer 145' above $T_g$, deforming the washer 145' into a new desired permanent shape, (e.g. a shape with a more suitable permanent diameter) and maintaining the washer 145' in that shape and at that temperature for a selected period of time. The heating time required to set the new permanent shape will depend on the particular polymer.

In FIGS. 11 and 12, the washer 145' is initially fabricated with a permanent shape such that the washer 145' has a relatively small diameter aperture 174 as shown in FIG. 12. Prior to insertion into the electrode 20, the washer 145' is heated above the glass transition temperature for the material used to fabricate the washer 145' and the washer 145' is mechanically deformed into the temporary shape shown in FIG. 11 so that the aperture 174 is large enough to readily accommodate the coils of the torque coil 48. After the electrode 20 has been secured to myocardial tissue, the washer 145' may be again heated above the glass transition temperature in situ so that the washer 145' returns to its permanent shape as shown in FIG. 12. The area of the aperture 174 decreases after transformation into the permanent shape.

Heating the washer 145' above the glass transition temperature may be accomplished by introducing a heated fluid into the bore 143, such as saline. It is anticipated that the permanent inner diameter of the aperture 174 may be fabricated small enough so that surface tension effects will restrict most if not all influx of body fluids past the washer 145'.

FIG. 13 illustrates another variation of the shape memory concept for the washer, now designated 145". In this embodiment, the washer 145" is fabricated with a permanent shape as shown in FIG. 13. However, prior to insertion into the electrode 20, the washer 145" is heated above the glass transition temperature and mechanically deformed into a more conventional shape, such as shown in FIG. 11. Subsequent to fixation to myocardial tissue, the washer 145" may be heated above the glass transition temperature so that the washer 145" returns to the permanent shape as shown in FIG. 13, and thereby provides a much greater restriction to the influx of body fluids past the washer 145".

Figure 14:
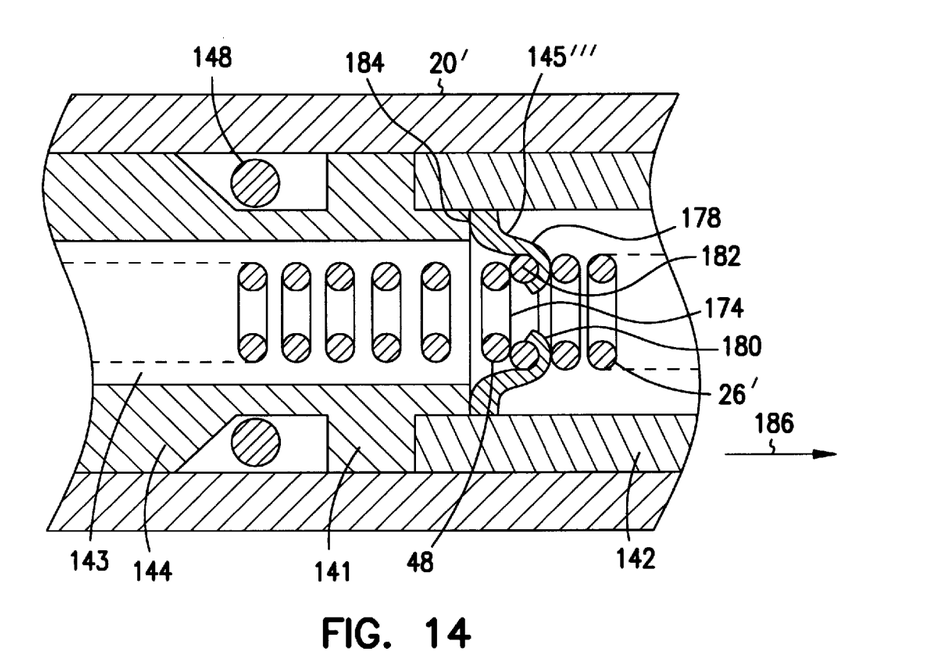
FIG. 14 is a cross-sectional view like FIG. 11 of another alternate shape-memory washer following in situ deformation in accordance with the present invention.
Figure 15:
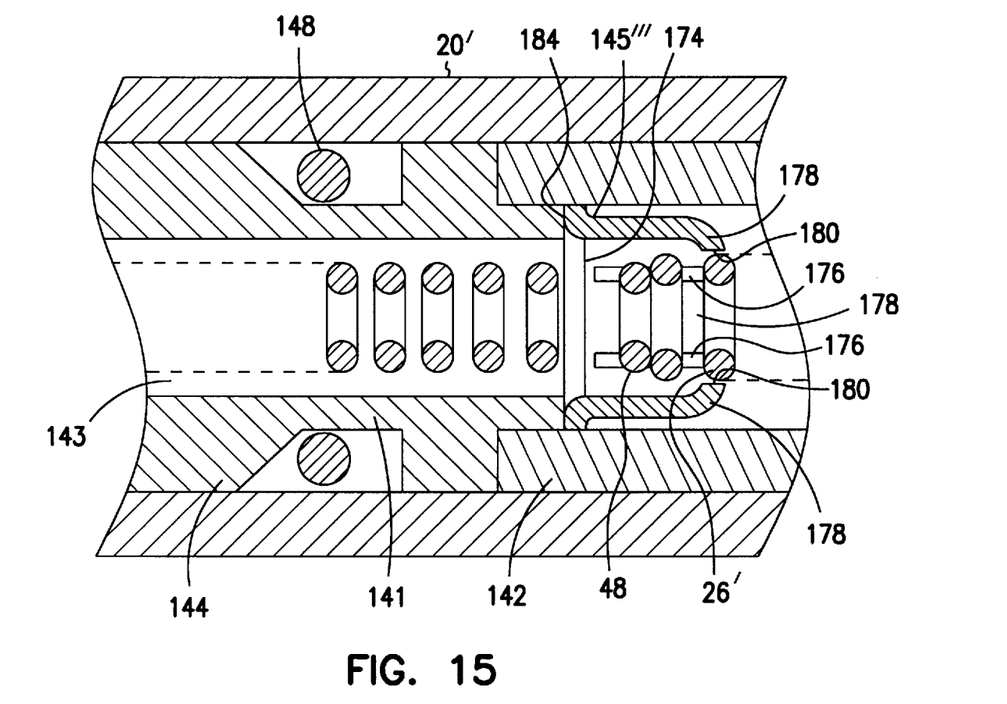
FIG. 15 is a cross-sectional view of the washer of FIG. 14 prior to in situ deformation in accordance with the present invention.
Figure 16:
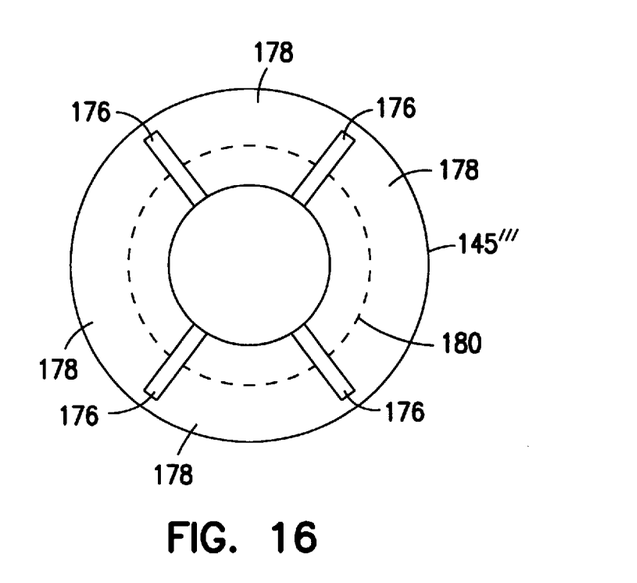
FIG. 16 is an end view of the washer of FIG. 15 in accordance with the present invention.

FIGS. 14, 15, and 16 illustrate another variation of the shape-memory concept for the washer, now designated 145''', suitable for use with an electrode-corkscrew combination where the corkscrew is not physically engaged to the electrode following deployment, such as the "smart" corkscrew 26' embodiment depicted in FIGS. 8, 9, and 10. In this embodiment, the washer 145''' is fabricated with the permanent shape shown in FIG. 14. FIGS. 15 and 16 depict cross-sectional and end views of the washer 145''' deformed into a temporary shape. Referring to FIGS. 15 and 16, the washer 145''' is fabricated as a conical-like structure with a plurality of peripherally spaced slots 176 that divide the washer 145''' into four collet-like fingers 178. Each finger 178 has a radially inwardly facing rim 180 that is designed to engage a coil of the corkscrew 26, such as the coil 182. Prior to insertion into the electrode 20, the washer 145''' is deformed into the temporary shape and secured to the shank 141 at 184 by a suitable medical grade adhesive of the types described above.

Following deployment of the corkscrew 26', the washer 145''' is heated in situ above the glass transition temperature $T_g$, causing the washer 145''' to deform back into the permanent shape shown in FIG. 14. As the fingers 178 curl inward, the rims 180 engage the coil 182 and exert a proximally oriented axial load. Since the washer 145''' is secured to the shank 141, the effect of the proximally oriented axial load on the corkscrew 26' is an axial thrust applied to the electrode 20 in the opposite direction, that is, a force that urges the electrode to move axially relative to the corkscrew 26 in the direction of the arrow 186 shown in FIG. 14. As a result, the electrode 20 is thrust against the myocardial tissue, providing reliable contact between the electrode 20' and the targeted tissue. Note that the thrusting action of the washer 145''' could be accomplished by eliminating the slots 176 so that the rims 180 are integral.

For long-term implantation, the washers 145', 145", and 145''' may be fabricated from heat-sensitive shape memory polymers such as polynorbornene supplied by Nippon Zeon of Japan, polyurethane supplied by Mitsubishi Heavy Industries of Japan, Calo.Mer™ supplied by Polymer Technology Group of California, or similar materials. If the lead 10 is designed for more transient implantation, materials such as polyvinyl chloride, or similar materials may be used in addition to the above-described materials.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac stimulator lead, comprising:
    a connector for connecting to a cardiac stimulator, and having a pin member rotatably coupled thereto;
    a tubular insulating sleeve having a first end coupled to the connector and a second end;
    an electrode coupled to the second end having a longitudinal bore, and a corkscrew coupled to the electrode and being projectable from and retractable into the bore, a portion of the electrode being radiopaque;
    a torque coil coupled between the pin member and the corkscrew;
    a radiopaque member coupled to the torque coil;
    a conductor wire disposed in the sleeve and coupled between the connector and the electrode for transmitting electric signals between the cardiac stimulator and the electrode; and
    the pin member comprising a notch formed in a distal end thereof, the connector further comprising a tubular connector insulating sleeve and a tubular contact sleeve coupled to the tubular connector insulating sleeve, the contact sleeve having a distally facing annular surface, the pin member being rotatably journaled in the insulating sleeve and being prevented from withdrawing from the insulating sleeve by engagement between the annular surface and the notch.

2. The cardiac stimulator lead of claim 1, wherein the torque coil comprises a coiled wire.

3. The cardiac stimulator lead of claim 2, wherein the coiled wire is composed of MP35N alloy.

4. The cardiac stimulator lead of claim 1, wherein the conductor wire comprises a metal conductor coated with an insulating material.

5. The cardiac stimulator lead of claim 1, wherein the electrode bore further comprises:
    a first longitudinal section having at least one internal thread and a second longitudinal section,
    the corkscrew disposed in the bore, the corkscrew having a first range of axial movement wherein the at least one internal thread is engaged, and a second range of axial movement wherein the at least one internal thread is not engaged, a portion of the corkscrew projecting from the second longitudinal portion in the second range of axial movement.

6. The cardiac stimulator lead of claim 5, wherein the means for rotating the corkscrew comprises a coiled wire having an end disposed in the bore and coupled to the corkscrew.

7. The cardiac stimulator lead of claim 5, comprising a washer disposed in the electrode for restricting the influx of body fluids therein, the washer having an aperture sized to accept the corkscrew.

8. The cardiac stimulator lead of claim 1, wherein the torque coil having a longitudinal torque coil bore, the radiopaque member comprising a slug and disposed within the torque coil bore.

9. A cardiac stimulator lead, comprising:
    a connector for connecting to a cardiac stimulator, and having a pin member rotatably coupled thereto;
    a tubular insulating sleeve having a first end coupled to the connector and a second end;
    an electrode coupled to the second end having a longitudinal bore, and a corkscrew coupled to the electrode and being projectable from and retractable into the bore;
    a torque coil coupled between the pin member and the corkscrew;
    a conductor wire disposed in the sleeve and coupled between the connector and the electrode for transmitting electric signals between the cardiac stimulator and the electrode;

the pin member comprising a notch formed in a distal end thereof, the connector further comprising a tubular connector insulating sleeve and a tubular contact sleeve coupled to the tubular connector insulating sleeve, the contact sleeve having a distally facing annular surface, the pin member being rotatably journaled in the insulating sleeve and being prevented from withdrawing from the insulating sleeve by engagement between the annular surface and the notch.

10. The cardiac stimulator lead of claim 9, further comprising a radiopaque member coupled to the torque coil.

11. The cardiac stimulator lead of claim 9, wherein the contact sleeve and the pin member are electrically conductive, the contact sleeve coupled to the conductor wire electrically coupling the conductor wire to the pin member through the engagement between the annular surface and the notch.

12. The cardiac stimulator lead of claim 11, further comprising a second conductor wire disposed in the tubular insulating sleeve and coupled between the connector and a second electrode, the second electrode coupled to the tubular insulating sleeve near the distal end and insulated from the first electrode, the connector further comprising an annular member, the annular member coupled to the insulating sleeve and electrically insulated from the tubular contact sleeve, the annular member having a distally projecting flag coupled to the second conductor establishing an electrical connection between the annular member and the second electrode for transmitting electric signals between the cardiac stimulator and the second electrode.

13. The cardiac stimulator lead of claim 9, wherein the first electrode further comprising:

a first tubular shank electrically coupled to the conductor wire;

a second shank electrically coupled to the first shank and sharing a common, centrally disposed bore, the second shank coupled to the corkscrew, the torque coil passing through the first tubular shank and coupled to the corkscrew.

14. The cardiac stimulator lead of claim 13, wherein the first tubular shank is radiopaque.

15. The cardiac stimulator lead of claim 13, wherein the second tube shank comprising a distal tip.

16. The cardiac stimulator lead of claim 15, wherein the distal tip comprising one or more slots.

17. The cardiac stimulator lead of claim 9, wherein the conductor wire is coupled to the pin member.

18. The cardiac stimulator lead of claim 9, wherein the torque coil comprising a coiled wire.

19. The cardiac stimulator lead of claim 18, wherein the coiled wire is composed of MP35N alloy.

20. The cardiac stimulator lead of claim 9, wherein the conductor wire comprising a metal conductor coated with an insulating material.

* * * * *